United States Patent [19]
Piva et al.

[11] Patent Number: 5,811,581
[45] Date of Patent: Sep. 22, 1998

[54] PROCESS FOR THE PURIFICATION OF OPACIFYING CONTRAST AGENTS

[75] Inventors: Rodolfo Piva; Carlo Felice Viscardi; Massimo Gagna, all of Milan, Italy

[73] Assignee: Dibra S.p.A., Italy

[21] Appl. No.: 804,118

[22] Filed: Feb. 20, 1997

Related U.S. Application Data

[63] Continuation-in-part of Ser. No. 456,763, Jun. 1, 1995, abandoned, which is a continuation of Ser. No. 285,783, Aug. 4, 1994, abandoned.

[30] Foreign Application Priority Data

Feb. 23, 1996 [IT] Italy .................................. MI96A0339

[51] Int. Cl.⁶ .......................... A61K 49/04; C07C 233/64
[52] U.S. Cl. .......................... 564/153; 210/635; 210/639; 424/9.35; 424/9.37; 424/9.43; 424/9.425; 424/9.454; 424/9.5; 536/55

[58] Field of Search ................................ 564/153; 536/55; 424/9.43, 9.452, 9.454, 9.35, 9.37, 9.5; 210/635, 659

[56] References Cited

U.S. PATENT DOCUMENTS

| | | | |
|---|---|---|---|
| 5,160,437 | 11/1992 | Bosworth et al. | 210/651 |
| 5,204,005 | 4/1993 | Doran et al. | 210/656 |
| 5,210,300 | 5/1993 | Kneller | 564/153 |
| 5,447,635 | 9/1995 | Viscardi et al. | 210/636 |

*Primary Examiner*—Richard L. Raymond
*Attorney, Agent, or Firm*—Nixon & Vanderhye

[57] ABSTRACT

A process for the purification of opacifying contrastographic agents, comprising chromatographic and nanofiltration techniques combined together, the subsequent chromatographic separation of the crude product solution and a nanofiltration step, with a final deionization on ion exchange resins.

11 Claims, No Drawings

PROCESS FOR THE PURIFICATION OF OPACIFYING CONTRAST AGENTS

CROSS-REFERENCE TO RELATED APPLICATIONS

This application is a continuation-in-part of Ser. No. 08/456,763, filed Jun. 1, 1995, now abandoned, which is a continuation of Ser. No. 08/285,783, filed Aug. 4, 1994, abandoned.

This invention refers to a process for the purification of neutral, water-soluble, non-ionic iodinated contrastographic agents for X-rays, directly applicable to raw reaction mixtures deriving from the synthesis.

This method is applicable on an industrial scale and can be used to obtain a commercial product with a very high degree of purities, characterized by a total impurity content well below the limits fixed by the Pharmacopoeia and the other recognized industrial production standards.

This result, which is extremely interesting from the medical point of view, has been obtained for the first time in an economic, ecologically safe manner, without affecting the global yield of the process.

The non-ionic types of iodinated opacifiers which can be purified by means of this new process include, for example, the following, tri- and hexa-iodinated monomers and dimers: Iopamidol, Iomeprol, Iopromide, Iohexol, Iopentol, Ioversol, Ioxitol, Iodixanol, Iotrolan, Iofratol, Iopyrol, and Metrizamide.

Although the purification process of the invention can be applied to a vast range of non-ionic water-soluble, tri- and hexa-iodinated opacifying agents, the following description—for simplicity and clarity of explanation, but not in a limiting manner for the skilled specialist—shall in particular refer to Iopamidol, or (S)—N,N'-bis[(2-hydroxy-1-(hydroxymethyl)- ethyl]-5-[(2-hydroxy-1-oxopropyl)amino]-2,4,6-triiodo-1,3-benzenedicarboxyamide, having the formula (I)

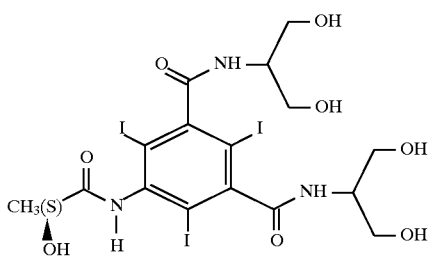

and also to Iomeprol, or [N,N'-bis(2,3-dihydroxypropyl)-5-[(hydroxy-acetyl)methylamino]-2,4,6-triiodo-1,3-benzenedicarboxyamide, having the formula

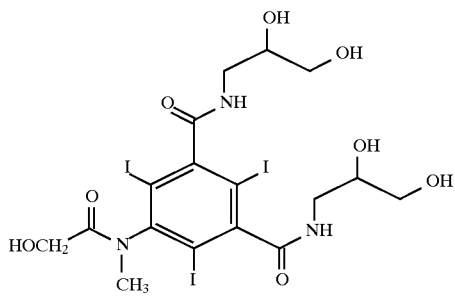

Iopamidol is one of the products most widely sold all over the world in the field of contrast media for X-rays. The methods of preparation and purification are described in various publications, including patents or patent applications like GB 1472050, U.S. Pat. No. 4,001,323, FR 2293919 and so on.

The processes mentioned give rise to a final raw product containing a certain number of impurities, ionic and non-ionic, by-products and unreacted intermediate products. As in the case of other non-ionic iodinated contrast agents, the final purification of the raw product is complicated, costly and difficult.

In fact the neutral opacifying compounds differ from the ionic ones, as they cannot be isolated and purified by precipitation with water, because of their very high solubility in this solvent.

One of the preferred techniques for the purification of these compounds consists in subjecting the final raw solutions of the contrast agent to a series of operations including the following:

preliminary removal of reaction organic solvents (dimethylacetamide, DMAC, in the case of Iopamidol) by evaporation, dilution of the residue with water, extraction of residual organic solvent with solvents immiscible with water (like methylene chloride or similar), elution of the aqueous solution on cationic and anionic ion exchange resins, eluate concentration, crystallization of the residue from the hydroalcoholic mixtures, to remove all traces of neutral impurities (as described in GB 1472050 and, more recently, in GB-A-2280436).

The drawbacks of these processes are numerous. For example, large plants are necessary for the purification on ion exchange resins, whose running costs are very high. It must also be remembered that concentration of the considerable volumes of water used demands a high consumption of thermal energy.

Finally, the prolonged thermal treatment of these solutions affects the quality of the finished product.

Other purification techniques have also been proposed recently. All these, however, generally aim at improving the economic aspect of the process and do not provide—nor suggest—indications regarding the final degree of purity of the product obtained.

U.S. Pat. No. 5,160,437, for example, describes the purification of raw Ioversol solutions by inverse osmosis; while the U.S. Pat. No. 5,210,300 patent suggests continuous deionization for purification of the same compound.

Neither of these two documents, however, contains experimental values regarding the process yield or the purity of the final product.

As regards Iopamidol, good progress has been made as regards economy and environmental impact (U.S. Pat. No. 5,447,635). This new process involves the techniques of tangential filtration through nano- or ultrafiltration membranes, making it possible to concentrate, desalinate and purify raw aqueous iopamidol solutions without resorting to extraction using solvents and using large quantities of ion exchange resins. However, the chemical purity of the final product is not substantially different from that obtained with the usual method (GB 1472050).

In connection with Iopamidol, GB-A-2287024 describes a variation of the technique described above, in which removal of reaction solvent, instead of using a solvent immiscible with water, is obtained by previously fixing Iopamidol on an anionic resin and then eluting it with a weak acid. This operation is made possible by the characteristic acidity of the proton present on the amido group in position 5 of the molecule's aromatic ring.

It is known that iodinated contrast agents can also be purified using preparative chromatography techniques (EP 83964, WO 8908101, DE 3110737, U.S. Pat. No. 5,204,005 and Skjold W., Berg A., J. Chromatogr. 366, (1986), 299–309): these techniques, however, usually give products with very high purity only under conditions that cannot be used on an industrial scale. In fact, it is well known that the quality of chromatographic separation depends, besides the intrinsic characteristics of the product and the impurities to be separated (impurities that are much more hydrophilic or lipophilic than the product can be separated more easily than impurities with lipophilicity similar to that of the product), also on the efficiency of the column (number of theoretical plates) and, to a certain extent, on the quantity of stationary phase used per gram of product loaded. It is known that preparative liquid chromatography systems have a much lower efficiency than the analytical ones, because of the different geometry of the column and the larger sizes of the particles forming the stationary phase. To this must be added the fact that it is not practical to operate with large quantities of stationary phase, not only because this reduces the productivity, but also because the volume of eluent to be used—and subsequently to be evaporated—to yield the product increases proportionally to the quantity of the stationary phase. As a result, in industrial systems, it is rarely possible to obtain complete separation of product and impurities with a single passage through the column. In the absence of complete separation, obtaining a very pure product can, in some cases, be impossible or, in other cases, be possible only on condition that the part (the front and/or tail) of the peak of the product which superimposes the impurities is rejected, thus affecting the yield of the product.

In a chromatographic system on a preparatory scale, if reduced quantities of stationary phase are used, the fraction of by-products removed is found to be fairly small and limited only to by-products which are more strongly adsorbed than the required product.

Recycling the rejected is usually expensive, not easy, and globally unsatisfactory.

The process described in the U.S. Pat. No. 5,204,005 clearly illustrates these limits: the low weight ratio between the stationary phase and the loaded substance (in the range 10:1 to 1.5:1) prevents an high degree of purity being obtained, in spite of the preventive desalination of the solution fed into the chromatography column.

Table 1 of the above-mentioned patent shows how the levels of purity obtained are always relatively small (the limits set on the two impurities taken into consideration are 0.1 and 0.50% respectively) and purification of the loaded substance is particularly limited. In the example in which the best level of purity is obtained, the quantity of stationary phase used compared with the raw material is larger than in the other cases (7:1 by weight); however, the product obtained still contains 0.3% of total impurities.

DE 3110737 describes a chromatographic purification method that is substantially similar to that of U.S. Pat. No. 5,204,005; in this case, the quantity of stationary phase used compared with the loaded product is relatively low (from 2:1 to 15:1 in weight); the scope of the invention is, however, only the elimination of ionic impurities.

As regards lipophilic impurities, in this case, (Examples 3 and 4 of the above-mentioned patent), the use of a relatively small quantity of stationary phase implies that reasonably high levels of purity can be obtained only by rejecting a significant fraction of the product fed to the column so that neither the yield nor the level of final purity is satisfactory.

In their above mentioned article, Skjold and Berg describe two cases of chromatographic purification on very high quantities of stationary phase (20 g of stationary phase/g of raw substance to be purified, ratio by weight of 20:1); the purity obtained is satisfactory but not exceptional (0.4% of residual impurities in the best cases); however, the recovery yield is quite low (72% in the most favourable cases).

On the whole, it may be concluded that, because of the problems concerning their scale-up, purification techniques are not currently available which consent to obtain non-ionic contrast agents with a total impurity content lower than 0.3% to be obtained on an industrial scale.

The problem of industrial production of non-ionic iodinated opacifying contrast agents for X-rays with a very high level of purity, particularly with a total impurity content lower than 0.5%, still remains unsolved.

For example, for compounds like Iopamidol or Iomeprol (described in patent EP 26281, Compound A of Table 1), or Iofratol (described in patent application WO 9208691), operating with the processes described in literature, the total impurity content is never found to be lower than 0.3%. Said in other words, the purity of said compounds has never reached levels higher than 99.7%.

The situation regarding other non-ionic iodinated contrast media on the market, or in advanced state of development, is substantially similar. In this regard, the following publications may be referred to: U. Speck's "X-ray Contrast Media: Overview, Use and Pharmaceutical Aspects", published by the Medical Division, Department of Medical Information, Schering, or Berg. A. and others, "Synthesis, analysis and toxicity of some compounds which may be formed during the synthesis of Iopentol", Acta Radiologica (1987) Suppl. 370, 27–31, or Skinnemoon K. and others, and "Formulation and Stability of Iopentol", idem, 37–40.

On the other hand, requests from the medical world and the bodies responsible for authorizing the marketing of drugs for the development of medicines with a very low impurity content is completely justified by the necessity to reduce to a minimum the risks to patients from secondary or toxic effects due to these medicines. In the case of iodinated contrast media, this request is particularly justified because the total quantity of product administered is larger than that of other medicines.

For example: the dose of opacifying agent administered may even exceed 150 g. As a result, 0.5% of by-products corresponds to administering at least 750 mg of impurities to the patient.

The purification method described in this invention makes it possible to give a positive response to the medical requirements outlined above, at the same time improving a number of parameters essential in the global evaluation of an industrial process. The total economy of management has undergone considerable improvement (significant energy saving, and almost complete removal of costs linked to the ion exchange resins and reagents necessary for their regeneration). Finally, the total yield of the process has remained practically unchanged.

By using the process of this invention, it is possible to obtain (among other iodinated non-ionic types of opacifier compounds for X-rays) Iopamidol and Iomeprol with a total impurity content that is considerably lower than 0.3%, preferably lower than 0.15% (the average content of these is about 0.1% or even less).

Besides, each individual impurity is found to be less than 0.1%—less than 0.05% on average.

These values are also lower than the current limits fixed by the FDA (Food and Drug Administration) below which it is not necessary to provide documentation regarding toxicity of impurities in the registration dossier of a drug.

Compared to the current state of the technique, the process described for this invention therefore makes it possible to obtain a considerable reduction in the impurities administered to patients (up to 80% less or even more).

The exceptional technical improvement made to the state of art by this invention is therefore quite clear.

The purification method involved in this invention consists of a specific integrated adoption of chromatographic and nanofiltration techniques, subjecting in sequence the solution of the raw product to chromatographic separation and to nanofiltration, with final deionization on ion exchange resins.

The initial chromatography, carried out at high or low pressure under reversed phase conditions on a column containing a hydrophobic stationary phase, provides a pre-purification that makes it possible to eliminate lipophilic impurities, which remain strongly absorbed compared to the other saline components and the hydrophilic product. In fact, the eluate coming out of the column can be divided into three fractions, or in three sub-fractions groups; the first contains the product, salts and unabsorbed hydrophilic impurities; the second contains the pure product diluted; and the third contains the absorbed lipophilic impurities which are rejected. The first fraction (taken as such or in subsequent portions) is supplied to the nanofiltration system and concentrated and desalinated; the second fraction (taken as such or in subsequent portions) is added to the first concentrated fraction (retentate) and again concentrated and desalinated by nanofiltration. Addition of the second fraction can be carried out without stopping the filtration, continuously or in stages. The final concentrated solution retentated in the nanofiltration unit (final retentate), obtained by the method of this invention, is surprisingly pure from salts and impurities, so that it can be completely deionized by contact with a very small amount of ion exchange resin.

The resulting concentrated, deionized solution contains the contrast agent in an almost pure form. From this, the solid substance can be separated by means of the usual methods like precipitation or evaporation of the solvent, and normally no further purification is necessary to obtain the required purity.

Application of this method involves first filling a conventional chromatographic column with a solid phase suitable for carrying out the required separation into the three fractions of eluate above described. The nature of the solid phase will obviously depend on the intrinsic properties of the substances to be separated, usually it is chosen from the various conventional phases known at present; the solid phase shall be chosen specifically for carrying out separations using reversed phase chromatography.

The solid phases usually preferred include the following: stationary phase consisting of RP18 or RP8 type silanized silica particles, a polystyrene based resin, a polyacrylic ester based resin, or a reticulated aliphatic polymer based resin.

Since the primary aim of this step is the elimination of lipophilic impurities (in fact, desalination and elimination of hydrophilic impurities having low molecular weight occurs substantially during the subsequent nanofiltration phase) the quantity of solid phase relative to the raw product to be purified can be very low, without invalidating the overall effectiveness of purification.

The ratio by weight of stationary phase to raw product loaded is in the range 20:1 and 2:1 (calculated on solids in solution).

However, according to this invention, this ratio can advantageously also reach values lower than 2:1 —for example, between 2:1 and 0.5:1 or even lower.

Once the column has been packed with the required solid phase, it is possible to supply the column with the mixture to be fractionated (usually in the form of an aqueous solution) and then elute the column to obtain the desired subsequent fractions.

The liquid eluent is also chosen depending on the requirements and according to the general knowledge in the field. Aqueous eluents are preferred, including pure water and/or aqueous solutions of salts, acids, bases or organic solvents miscible in water such as alcohols with a low number of carbon atoms, acetone, tetrahydrofuran, dioxane and similar liquids and/or their mixtures.

The eluent flow is monitored using conventional methods for identifying the points of separation between the fractions, so that each fraction can be collected separately. These techniques (for example, based on the measurement of parameters such as absorbance, optic activity, electrical conductivity, refractive index, etc.) are well known to specialists and require no further detailed explanation.

The various eluted fractions are subjected to nanofiltration according to the method described above, using—for example—a conventional tangential nanofiltration unit provided with a "low cut-off" membrane. The degree of porosity of the membrane and the working conditions (temperature, flow, ratio between flows of permeate and of loaded solution) are chosen depending upon the operator's needs and judgment. Membranes are normally used having a porosity such as to allow low molecular weight impurities and salts to pass through, while the required compounds are held back. The type of system and the relative process described in U.S. Pat. No. 5,447,635 are found to be particularly suitable for this type of operation.

The fractions are fed to the nanofiltration unit in the order in which they are eluted by the column or in decreasing order of concentration of salts and/or low molecular weight impurities. In this way, most of the salts and low molecular weight impurities are removed during nanofiltration so that the solution retained in the nanofiltration system at the end of the operation (final retentate) is not only found to be more concentrated, but is practically free of salts and low molecular weight impurities.

As a result, this purified solution can be completely deionized using conventional types of ion exchange resins (for example, mixed or separate beds of anion and cation resins) in quantities dramatically smaller than those used in state of the art purification methods, thus bringing about a net reduction in the costs involved in the deionization step.

This unexpected advantage of the invention is a significant step forward in the state of art. After deionization, the solution contains the opacifier compound in a practically pure form, allowing separation to be carried out using one of the traditional methods.

The integrated process forming the invention can be advantageously conducted continuously to optimize times. The eluate fractions from the chromatographic column are directly fed to the nanofiltration system and nanofiltration is carried out without interruption until the desired degrees of desalination and concentration are reached.

Alternatively, the process can be carried out in successive steps. The choice of the preferred process shall be decided by such parameters as type of solution to be purified, type and dimensions of the plant available, and the size of the production batch to be treated.

By applying the method described in this invention, there are considerable savings in terms of equipment, total process time, costs of materials to be supplied, while at the same time, better products are obtained, through better processes and with a global process yield substantially identical to those of the best process usually adopted. As mentioned earlier, the entire process can also be carried out using an integrated type apparatus, that is, the chromatographic column can be directly connected to the nanofiltration unit, thus obviating the collection and storage of large volumes of eluted fractions and reducing the times required for the process.

The experimental section contains a description of the preparation of very pure Iopamidol according to the method of this invention.

The raw Iopamidol solution subjected to purification was obtained by the method described in patent GB 1472050.

Iopamidol is synthesized by condensation between (S)-5-[(2-acetyloxy)-1-oxopropyl)amino]-2,4,6-triiodo-1,3-benzenedicarboxylic acid dichloride and 2-aminopropan-1,3-diol (serinol) in dimethylacetamide and subsequent saponification of the acetic ester obtained; most of the reaction solvent is removed by distillation; the distillation residue diluted with water forms an aqueous solution of the raw product which is sent for purification. In the course of the above reactions, a group of by-products are inevitably produced, some of which have unknown structures; other by-products are derived from the impurities of the substrate, solvent or serinol.

As described earlier in more general terms, the purification of this invention consists of the integrated coupling of a liquid chromatography system at low or high pressure, with a nanofiltration unit and a mini system of ion exchange resins.

The chromatographic system has the scope of removing lipophilic impurities during the passage of the raw product through the column by elution with water or a water-methyl alcohol solution. Because of the relatively low efficiency of the preparatory chromatographic system, as above described, separation of salts and product is not net (and does not, in any case, represent the scope of this step): in fact the first aqueous or hydro-alcoholic fraction eluted from the column contains the product, salts, traces of dimethylacetamide; a second fraction, on the other hand, consists of highly diluted Iopamidol devoid of salts.

The change of fraction can be decided on the basis of the conductivity value of the eluate. The first fraction is fed (completely or in small amounts) to a nanofiltration unit equipped with a semi-permeable membrane characterized by rejection to sodium chloride less than 85% and by a rejection to raffinose higher than 90% where it is concentrated: simultaneously, a part of the salts and impurities having low molecular weight is removed, passing through the membrane along with the water. At the end of the concentration of the first fraction, the loading of the second fraction begins (continuously or in successive amounts); the scope of this second phase is that of putting together the two fractions of the product as well as washing (diafiltration step) the first fraction concentrate which is still relatively rich in salts and permeable impurities, with the second fraction which is practically free of salts and impurities.

In this way there is no need to dilute the concentrate derived from the first fraction with more water (classical diafiltration phase) to be able to then bring the solution to the desired degree of purity. Obviously, only in case of particularly dirty initial raw solutions, a final phase of diafiltration with pure water may be necessary. In any event, the quantity of water used is minimum and not large enough to influence the global costs of the process.

The nanofiltration unit should preferably be constructed according to U.S. Pat. No. 5,447,635. When the entire second fraction has been fed and concentrated, nanofiltration is stopped and the final retentate is found to consist of a concentrated Iopamidol solution (approximately between 10 and 50% p/p) and is substantially free of impurities and salts.

This solution is percolated on a small quantity of cationic and anionic ion exchange resins (in series or in mixed bed) to remove the residual ionic impurities (triiodoisophthalic acids) and salts. The product can finally be isolated from the solution percolated through ion exchange resins by insolubilization from water-alcoholic mixture or directly by evaporation of the solvent.

The content of by-products and impurities in Iopamidol is determined by the HPLC method described below:

1 Test solution 1 g of Iopamidol to be analyzed is accurately weighed, dissolved in deionized water and diluted to volume in a 100 ml volumetric flask.

2 Standard solution 10 mg of standard Iopamidol are dissolved in deionized water and diluted to 1000 ml (0.1% concentration of the sample being analyzed).

3 Procedure 20 ml of the test solution and standard solution are injected into a liquid chromatograph, operating under the following conditions:

Apparatus: high pressure liquid chromatograph Hewlett-Packard 1084B or similar

Column: LICHROSORB RP 18, $5\mu$, diameter 4 mm, length 25 cm or similar

Eluents:
A=water
B=25% methyl alcohol (v/v) in water

| Gradient: | |
|---|---|
| Time (minutes) | % B |
| 0 | 7.5 |
| 6 | 7.5 |
| 18 | 35.0 |
| 30 | 92.0 |
| 34 | 92.0 |
| 37 | 7.5 |
| 42 | 7.5 |

Flow: 1.5 ml/min

Oven temperature: 35° C.

Detection: 240 nm

Calculation of by-products

Each by-product is calculated relative to 0.1% of glycolic derivative:

$$\% \text{ of each by-product} = \frac{\text{area of by-product} \times 0.1}{\text{Area of glycolic derivative}}$$

The minimum limit that can be detected for each by-product is 0.005%.

The total content of by-products is given as the total of the individual percentages.

The quantity of aromatic amines is determined by the method described in Iopamidol, Official Monographs, USP XXII.

The commercial Iopamidol obtained by this method has a very high degree of purity; the total impurity content is about 0.15% on average, usually not higher than 0.1%. Each impurity—in those cases where it can be measured using standard analytical methods—is found to be lower than 0.1%, usually about 0.05%. In particular, among the individual impurities, the content of free aromatic amines does not exceed 0.01%; it is found to be lower than 0.005%.

Similarly, by means of the process of this invention, it is possible to purify the reaction mixture resulting from the Smiles type of intramolecular rearrangement which, in an aqueous alkaline medium, leads to another non-ionic iodinated contrast agent, Iomeprol. This preparation is described in patent EP 365541. The raw Iomeprol solution obtained by this process contains, besides the desired product, also the unreacted starting substrate (~1.5%), ionic and non ionic organic impurities (5–10%) and inorganic salts.

By applying the method of this invention, a concentrated Iomeprol solution is obtained which has a very high degree of purity, from which the contrast agent can be recovered by adding insolubilizing solvents, such as inferior alcohols, or directly by evaporation of the solvent, for example by "spray drying".

In order to measure the by-products and residual impurities content, the same HPLC method described above for Iopamidol is used, changing only the column temperature, which must be 60° C. The total impurities content in Iomeprol is found to be less than 0.15% in weight, usually less than or equal to 0.1%.

The said process is found to be particularly suitable also for purifying process solutions containing the non ionic hexaiodinated dimer, Iofratol (obtained as described in patent EP 557345), for which the total residual impurities content does not usually exceed 0.3%.

Some examples of preparation according to the method of this invention are described below.

EXAMPLE 1

In accordance with the process described in patent GB 1472050, 1.28 kg of serinol (14 mol) are dissolved in 4.8 kg of dimethylacetamide and poured into a solution obtained by dissolving 2.4 kg of (S)-5-[(2-(acetyloxy)-1-oxopropyl) amino]-2,4,6-triiodo-1,3-benzenedicarboxylic acid dichloride (3.38 mol) in 4.8 kg of dimethylacetamide, keeping the temperature below 35° C. On completion of the addition, the reaction mixture is kept under agitation for 8 hours at about 20° C. Most of the reaction solvent is distilled out at 95° C. and 10 mbar until a viscous residue is obtained, which is diluted with 6 kg of hot deionized water. The solution obtained, which contains more than 99% of the product, is brought to 35° C.: at this temperature, 1 kg of 30% p/p sodium hydroxide is added and the solution is kept under agitation for 7 hours to obtain saponification of acetic ester of acetyl-Iopamidol. The solution is then acidified at pH 6.5 with 0.44 kg of 34% p/p hydrochloric acid to stop saponification and the raw Iopamidol solution thus obtained—containing Iopamidol (about 2.55 kg), related ionic and non ionic substances in quantities equal to about 3% of the product, NaCl (about 240 g), 860 g of serinol hydrochloride, about 300 g of DMAC (dimethylacetamide) and 280 g of sodium acetate—is fed at a flow rate of 25 L/h to a column containing 5 l of Rohm and Haas Amberlite XAD1600 resin previously regenerated with 12 kg of a 1:1 water:methyl alcohol solution and conditioned with 20 l of deionized water. The eluate from the column is rejected until the UV detector detects the presence of product in the eluate (rejected fraction: 1 kg) then it is collected in the nanofiltration tank described in Example 2, which is started up as soon as the level in the tank is sufficient. At the end of the loading phase, the product remaining in the column is eluted with 30 kg of an 0. 0055M NaOH solution and the eluate is sent to the nanofiltration tank.

At this point, the UV detector shows that the quantity of product contained in the eluate is reduced (about 5 g/kg) and the elution is stopped. When the solution contained in the nanofiltration unit is reduced to about 12 kg, nanofiltration is also stopped. The retentate contains 2.49 kg of Iopamidol, small quantities of ionic impurities and dimethylacetamide, and less than 0.2% of non ionic substances compared to Iopamidol. This solution is then percolated on a series of three columns containing 1 l of Rohm and Haas Amberjet 1200 sulphonic resin in hydrogen form, 1 l of weak anionic Relite MG1 resin in the free base form and 200 ml of Amberjet 1200 resin in hydrogen form respectively, and the eluate is collected: the columns are then rinsed in series with 4 l of water and the eluate is added to that of the previous phase. The solution obtained containing practically pure Iopamidol is thermally concentrated to obtain a viscous residue; the residue is refluxed at atmospheric pressure and diluted by slowly adding 8.6 kg of 2-butyl alcohol, keeping the solution under reflux: before the end of the addition, the product precipitates in crystalline form.

At the end of the addition, the solution is cooled to 20° C., the solid is separated by centrifuging and the panel is rinsed with 1.5 kg of 2-butyl alcohol. After drying, 2.40 kg of Iopamidol are obtained (91% of theoretical) containing 0.15% of total related impurities, free from aromatic amines.

EXAMPLE 2

A quantity of 18 l of raw Iopamidol solution obtained by the method described in Example 1 and containing 3.78 kg of Iopamidol, about 3% of ionic impurities (triiodoisophthalic acids), about 0.8% of non ionic impurities as well as NaCl and sodium acetate (about 15%), 2-aminopropan-1,3-diol, dimethylacetamide (about 20%), is fed by means of a triplex pump having a capacity of 700 L/h into a column having an internal diameter of 450 nm containing about 48 kg of E. Merck Lichroprep$^{(R)}$ RP18 40–63 μm silanized silica (counterpressure: 40 bar). On completion of loading, elution is carried out with deionized water: the eluate passes into a flow-through cell for continuous measurement of conductivity and in a flow-through spectrophotometric detector operating at 280 nm and is sent for discharging. After about 20 l of washing, the output signal from the spectrophotometer starts increasing because of the presence of iodinated compounds in the eluate: the eluate from this moment is collected in fraction 1. After a further 120 l the conductivity value falls below 2 mS/cm: the eluate from this moment is collected in fraction 2. Collection of the eluate in fraction 2 continues until absorbance falls below the value corresponding to 1 g/L: fraction 2 is found to consist of 400 L. The column is then regenerated with 80 l of methyl alcohol and finally conditioned with 80 l of deionized water. The process lasts an hour. Fraction 1 is fed to a nanofiltration unit consisting of a 50 l tank, a triplex pump capable of delivering 1800 L/h at 4 MPa, a FILMTEC $^{(R)}$ NF404040 (7 m$^2$) module, a counterpressure valve and a 450 cm$^2$ coaxial pipe exchanger (process in the pipe and cooling water in the jacket). The process solution output from the exchanger is recirculated to the tank. Fraction 1 is concentrated to 50 L; fraction 2 is then fed at such a flow as to maintain the tank volume constant. When the entire fraction 2 has been fed, the process is continued until the tank volume is reduced to about 15 L: the solution obtained contains 3720 g of Iopamidol (yield 98.5%) with about 3% of ionic impurities and practically free of other impurities. The product is then percolated on a Rohm and Haas Duolite C20MB and Relite MG1 ion exchange resin (each 1500 ml) battery to remove ionic impurities: the resin eluate (20 L) is concentrated to a viscous residue and insolubilized with 2-butyl alcohol. 3600 g of Iopamidol (yield 95%) are obtained, containing 0.05% of total impurities, almost devoid of free aromatic amines and with color 0.004 µA. The total productivity per volume is equal to almost 90 kg/d. The productivity of the column is about 1 kg/d $1_{column}$).

EXAMPLE 3

6 l of the same raw Iopamidol solution as described in Example 1 are fed at a flow of 70 L/h to a column containing 20 l of Rohm and Haas XAD7 polyacrylic adsorbent resin. The eluate passes into a flow-through cell for continuous measurement of the conductivity and into a flow-through spectrophotometric detector operating at 280 nm and is then sent for discharge. The solution is then eluted at the same flow with deionized water. After about 3 l of washing the output spectrophotometer signal starts increasing indicating the presence of iodinated compounds in the eluate: the eluate is from this moment on collected in fraction 1. After a further 25 L, the conductivity value falls below 2 mS/cm: the eluate from this moment is collected in fraction 2: collection of eluate in fraction 2 continues until absorption falls below a value of 2 g/L. Fraction 2 is found to contain about 70 L. Fraction 1 is fed to a nanofiltration unit consisting of a 6 l tank, a triplex pump capable of delivering 700 L/h at 4 MPa, a FILMTEC$^{(R)}$ NF402540 (7 m$^2$) module, a counterpressure valve and a 150 cm$^2$ coaxial pipe exchanger (process in the pipe and cooling water in the jacket). The process solution output from the exchanger is recirculated to the tank. Fraction 1 is concentrated to 6 L; fraction 2 is then fed at such a flow as to maintain the tank volume constant. When the entire fraction 2 has been fed, the process is continued until the tank volume is reduced to about 4 L: the solution obtained contains 1240 g of Iopamidol (98.5%) with about 3% of ionic impurities and is practically free from other impurities. The product is then percolated on a Rohm and Haas Duolite C20MB and Relite MG1 ion exchange resin (each 500 ml) battery to remove ionic impurities: the resin eluate (7 L) is concentrated to a viscous residue and insolubilized with 2-butyl alcohol. 1190 g of Iopamidol (94%) are obtained, containing 0.1% of total impurities, of which 0.005% are made up of free aromatic amines.

The chromatography column is regenerated by passing a solution containing 50% methyl alcohol in countercurrent at a flow of 70 L/h, and then 50 l of water at the same flow rate but in equicurrent (from above).

The entire cycle lasts three hours, like the entire nanofiltration process: productivity of the system is therefore about 10 kg/d. The productivity per unit volume of the column is found to be about 0.5 kg/(d $1_{column}$).

EXAMPLE 4

A quantity of 6 l of the same raw Iopamidol solution as described in Example 1 is fed at a flow rate of 70 L/h to a column containing 15 l of Rohm and Haas XAD16 polystyrenic adsorbent resin; the procedure is continued as in Example 2, the only difference being that the washing is increased such that fraction 2 consists of 150 l instead of 70 L. The process downstream does not change, except for the final separation, which is carried out by insolubilization with 2-butyl alcohol. The purification yield on the column is 97.5%: 1170 g of Iopamidol are obtained (93%) with a total by-product content of 0.1% of which 0.007% are free aromatic amine.

The productivity is approximately the same as that of the previous example.

EXAMPLE 5

A quantity of 0.6 l of the same raw Iopamidol solution as described in Example 1 is fed at a flow rate of 60 L/h to a column having an internal diameter of 100 mm, containing 3 l of Tosohaas Amberchrom™ CG71cd polyacrylic resin (counterpression about 1 bar). On completion of loading, the solution is eluted with deionized water: the eluate passes into a flow-through cell for continuous measurement of conductivity and into a flow-through spectrophotometer detector operating at 280 nm and is sent for discharging. After about 1 l of washing, the spectrophotometer's output signal starts increasing because of the presence of iodinated compounds in the eluate: from this moment on the eluate is collected in fraction 1. After a further 5 L, the conductivity value falls below 2 mS/cm: the eluate from this moment on is collected as fraction 2: collection of the eluate in fraction 2 continues until the absorbance is reduced below the value of 2 g/L: fraction 2 is found to consist of about 10 L. The column is then regenerated with 5 l of methyl alcohol and then conditioned with 5 l of deionized water. The entire process, which has a duration of 30 minutes, is repeated 10 times on 10 batches of 0.6 l of the same raw Iopamidol solution. The union of the fractions 1 is fed to a nanofiltration unit consisting of a 6 l tank, a triplex pump capable of delivering 700 L/h at 4 MPa, a FILMTEC$^{(R)}$ NF402540 (2 m$^2$) module, a counterpressure valve and a 150 cm$^2$ coaxial pipe exchanger (process in the pipe and cooling water in the jacket). The process solution coming out of the exchanger is recirculated to the tank. The fractions 1 union is concentrated to 6 L; the union of fractions 2 is then fed at such a rate as to maintain the tank volume constant at about 4 L: the solution obtained contains 1230 g of Iopamidol (97.5%), 3% of ionic impurities and is practically devoid of other impurities. The product is percolated on a battery of Rohm and Haas Duolite C20MB and Relite MG1 ion exchange resins (500 ml of each) to remove the ionic impurities: the resins eluate (7 L) is concentrated to a viscous residue and insolubilized with 2-butyl alcohol. 1160 g of Iopamidol are obtained with a total by-product content of 0.1%, of which 0.005% is free aromatic amines.

The total productivity is equal to about 6 kg/d. The productivity per volume of the column is found to be equal to that of Example 1, in spite of the low load on the column.

EXAMPLE 6

A quantity of 20 l of a solution containing raw Iomeprol (obtained according to the method described in patent EP 365541) is brought to a pH of 10 with HCl and subjected to purification. This solution contains 3.50 kg of Iomeprol and the following by-products and impurities (% weight of Iomeprol): starting substance 1.4%; ionic impurities about 5%; non ionic impurities about 1%; about 7% NaCl. The solution is fed by a triplex pump (700 L/h) to a chromatographic column having an internal diameter of 450 mm, containing approximately 48 kg of Lichroprep(R) RP18 40–63 µm (E. Merck) silanized silica (counterpressure: less than 40 bar).

After loading, the solid phase is eluted with deionized water. The eluate first passes into a flow-through cell in which the liquid's conductivity is continuously measured, then through a spectrophotometric detector at 280 nm. After 30 l of eluate have been allowed to flow through, the spectrophotometer indicates the presence of iodinated compounds in the eluate. From this point onwards, the eluate forms fraction 1. After 120 l of eluate have flowed through, the conductivity falls below 2 mS/cm, indicating that fraction 1 is finished. From this moment on, the eluate is collected as fraction 2. The collection stops when the optic absorbance falls below the value corresponding to a concentration of 1 g/L. Fraction 2 is found to contain approximately 1000 l of liquid.

The column is then regenerated with 80 l of methyl alcohol and then conditioned with 80 l of deionized water. The process has a duration of 2 hours.

Fraction 1 is fed into a nanofiltration unit consisting of a 20 l tank, a triplex pump capable of delivering 1800 L/h at 4 MPa, a FILMTEC$^{(R)}$ NF402540 (7 m$^2$) module, a counterpressure valve and a 450 cm$^2$ coaxial pipe exchanger. The process solution coming out of the exchanger is recirculated to the tank.

The union of fractions 1 is concentrated to 20 L; the union of fractions 2 is then fed at such a rate as to maintain the tank volume constant. When the entire fraction 2 has been fed, the process is continued until the tank volume is reduced to about 10 L.

The solution obtained contains 3450 g of Iomeprol (98%), with 3% of ionic impurities, and is practically devoid of other impurities.

The product is then percolated on a mixed bed of ion exchange resins consisting of 0.5 l of Rohm and Haas Amberjet$^{(R)}$ 1200 and 1 l of Amberjet$^{(R)}$ 4200, to remove ionic impurities. The resin eluate (15 L) is concentrated to a viscous residue of 4 kg. This solution is allowed to drip into 25 l of 2-butyl alcohol, cooled to 20° C., filtered and dried. 3.38 kg of practically pure (Yield: 96%, Iomeprol) Iopamidol are obtained.

The analysis shows that the total content of impurities is 0.1%.

We claim:

1. A method for purifying iodinated, nonionic opacifier x-ray contrast agents having a global impurity content of not higher than 0.3% comprising the steps of:
   (a) loading a raw contrast agent solution on a chromatographic column containing a stationary hydrophobic phase;
   (b) eluting a first fraction, or group of fractions, containing the contrast agent and hydrophilic impurities;
   (c) eluting a second fraction, or group of fractions, containing the diluted, substantially pure contrast agent;
   (d) concentrating and simultaneously partially desalinating and purifying the first fraction, or group of fractions, in a tangential filtration system equipped with nanofiltration membranes with rejection of raffinose higher than 90% and rejection of sodium chloride less than 85%;
   (e) adding, continuously, or in parts, the second fraction, or group of fractions, to the concentrated retentate derived from step (d) in the same tangential filtration system to reunite the product initially contained in the two fractions coming from steps (b) and (c) into a single solution with reduced volume, containing the contrast agent and traces of ionic impurities; and
   (f) completing deionization of the concentrated solution by passing it through one or more columns containing anionic and cationic ion exchange resins to produce an iodinated, non-ionic opacifier x-ray contrast agent having a global impurity content not higher than 0.3%.

2. A method according to claim 1, in which chromatographic separation of steps b) and c) are carried out at high or low pressure.

3. A method according to claim 1, in which the stationary phase of the chromatographic column consists of Type RP18 or RP8 silanized silica particles, a polystyrene based resin, a polyacrylic ester based resin, or a reticulated aliphatic polymer resin.

4. A method according to claim 1, in which in step a) the ratio by weight between the stationary phase and the fed raw product ranges between 20:1 and 2:1.

5. A method according to claim 1 in which, in step a), the ratio by weight of the stationary phase and the fed raw product ranges between 2:1 and 0.5:1.

6. A method according to claim 1 in which each step is carried out in succession so that the first fraction b) is first subjected to nanofiltration and then the second fraction b) is added to the retentate obtained, resuming the nanofiltration until the final concentrated solution is obtained.

7. A method according to claim 1 in which the steps are carried out in continuously so that each fraction or subfraction is directly fed to the nanofiltration system and said nanofiltration is not stopped until the final concentrated solution is obtained.

8. A method according to claim 1 in which the purified contrast agent has a global impurities content not higher than 0.15%.

9. Purification method according to claim 1 in which the non ionic iodinated agent is Iopamidol.

10. Purification method according to claim 1 in which the non ionic iodinated agent is Iomeprol.

11. Purification method according to claim 1 in which the non ionic iodinated agent is Iofratol.

* * * * *